(12) United States Patent
Han et al.

(10) Patent No.: US 11,432,727 B2
(45) Date of Patent: Sep. 6, 2022

(54) SPO2 MINIPROGRAM: AI SPO2 MEASUREMENT APP

(71) Applicant: TENCENT AMERICA LLC, Palo Alto, CA (US)

(72) Inventors: Lianyi Han, Palo Alto, CA (US); Chao Huang, Palo Alto, CA (US); Xiaozhong Chen, Cedarburg, WI (US); Zhimin Huo, Palo Alto, CA (US); Shih-Yao Lin, Palo Alto, CA (US); Hui Tang, Mountain View, CA (US); Tao Yang, Mountain View, CA (US); Kun Wang, San Jose, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 226 days.

(21) Appl. No.: 16/869,740

(22) Filed: May 8, 2020

(65) Prior Publication Data

US 2021/0345892 A1  Nov. 11, 2021

(51) Int. Cl.
*A61B 5/1455* (2006.01)
*A61B 5/0205* (2006.01)
*G06K 7/14* (2006.01)
*G06K 7/10* (2006.01)
*G06F 17/18* (2006.01)
(Continued)

(52) U.S. Cl.
CPC .......... *A61B 5/0205* (2013.01); *A61B 5/0261* (2013.01); *A61B 5/14552* (2013.01); *A61B 5/6826* (2013.01); *A61B 5/6898* (2013.01); *A61B 5/742* (2013.01); *G06F 3/14* (2013.01); *G06F 17/18* (2013.01); *G06K 7/10722* (2013.01); *G06K 7/1413* (2013.01); *G06K 7/1417* (2013.01); *G06Q 50/01* (2013.01); *H04N 5/23203* (2013.01); *A61B 2560/0431* (2013.01)

(58) Field of Classification Search
CPC ... A61B 5/0205; A61B 5/0261; A61B 5/1455; A61B 5/14552; A61B 5/742; A61B 5/6826; A61B 5/6898
See application file for complete search history.

(56) References Cited

U.S. PATENT DOCUMENTS

| 2015/0190077 | A1 | 7/2015 | Kim et al. |
| 2018/0214088 | A1 | 8/2018 | Newberry |
| 2019/0313907 | A1 | 10/2019 | Khachaturian et al. |

FOREIGN PATENT DOCUMENTS

| CN | 105748053 A | 7/2016 |
| CN | 108520776 A | 9/2018 |

OTHER PUBLICATIONS

International Search Report dated May 25, 2021 in Application No. PCT/US21/20832.
(Continued)

*Primary Examiner* — Marjan Fardanesh
(74) *Attorney, Agent, or Firm* — Sughrue Mion, PLLC

(57) ABSTRACT

There is included an apparatus and system including video capture code configured to control a camera of a mobile phone to capture a video of at least a portion of skin, extraction code configured to extract at least one photoplethysmogram (PPG) signal from the video, determination code configured to determine a peripheral oxygen saturation (SpO2) value based on the PPG signal with respect to a blood flow at the portion of skin, and display code configured to control a display of the mobile phone to display the SpO2 value.

20 Claims, 4 Drawing Sheets

(51) Int. Cl.
*G06Q 50/00* (2012.01)
*G06F 3/14* (2006.01)
*A61B 5/026* (2006.01)
*A61B 5/00* (2006.01)
*H04N 5/232* (2006.01)

(56) References Cited

OTHER PUBLICATIONS

Written Opinion of the International Searching Authority dated May 25, 2021 in Application No. PCT/US21/20832.

SPO2 MINIPROGRAM: AI SPO2 MEASUREMENT APP

BACKGROUND

1. Field

The disclosed subject matter relates to systems for plethysmography and oxygen saturation analysis.

2. Description of Related Art

Related art is incapable of adequately bridging gaps between medical analysis and the general public, and tests for various health parameters and recommendations with respect to those tests are not easily accessible.

As such, there is insufficient early detection of parameters including deteriorated lung function and monitoring of oxygen saturation related symptoms, such as pneumonia or sports related health conditions.

SUMMARY

There is presently presented an a peripheral oxygen saturation, SpO2, measurement system, deployed such as via a miniprogram, which may help with the early detection of the deteriorated lung function and monitoring oxygen saturation related symptoms, such as pneumonia or sports related health conditions. The readily available modern mobile phones and the ever-increasing power of the peripheral capability for image analysis that is embedded within a social app as a hybrid web application, including elements of native and web applications, make it much easier to reach to the users as a quick and handy way for health condition evaluation. By considering the usability, accessibility and accuracy, embodiments described herein may provide user SpO2 estimates by utilizing the mobile phone camera and a social app.

There is described herein an optical plethysmogram, PPG, signal that can be used to measure blood volume changes in the microvascular bed of tissues. A PPG signal may be obtained by using a pulse oximeter which monitors the perfusion of blood to the dermis and subcutaneous tissues of the skin, and the PPG signal may be used to subsequently estimate the amount of oxygen in the blood, which is reported as SpO2. However, instead of using pulse oximeters, embodiments herein describe alternative approaches to measuring SpO2 that take advantage of modern mobile phones and a social media app by using the video capture functionality and frame by frame analysis of the captured video. Such solutions provide a reasonable approximation of the SpO2 measurement and does not require external hardware for the user other than a modern cell phone and social app.

According to exemplary embodiments, there is an apparatus and a method including at least one memory configured to store computer program code, and at least one hardware processor configured to access said computer program code and operate as instructed by said computer program code. The computer program code including: video capture code configured to cause the at least one hardware processor to control a camera of a mobile phone to capture a video of at least a portion of skin, extraction code configured to cause the at least one hardware processor to extract at least one photoplethysmogram (PPG) signal from the video, determination code configured to cause the at least one hardware processor to determine a peripheral oxygen saturation (SpO2) value based on the PPG signal with respect to a blood flow at the portion of skin, and display code configured to cause the at least one hardware processor to control a display of the mobile phone to display the SpO2 value.

According to exemplary embodiments, the apparatus and the method comprise the computer program code which further comprises social media app code configured to cause the at least one hardware processor to request a miniprogram from an external server, wherein the miniprogram comprises the video capture code, the extraction code, the determination code, and the display code.

According to exemplary embodiments, the apparatus and the method comprise scanning code configured to cause the at least one hardware process to control the camera to scan a code and to implement, in response to scanning the code, the social media app code configured to cause the at least one hardware processor to request the miniprogram from an external server, and the miniprogram comprises a model-view-viewmodel.

According to exemplary embodiments, the apparatus and the method comprise the computer program code which further comprises analysis code configured to cause the at least one hardware processor to implement a statistical processing of the PPG signal and to implement determining whether to at least one of alter and remove a portion of the PPG signal based on a result of the statistical processing.

According to exemplary embodiments, the statistical processing comprises determining a number of at least one of peaks and valleys of the PPG signal within a predetermined time among a plurality of frames of the video.

According to exemplary embodiments, the statistical processing comprises determining a variance of at least one of a peak and a valley of the PPG signal among a plurality of peaks and valleys of the PPG signal within a predetermined time among the plurality of frames of the video.

According to exemplary embodiments, the apparatus and the method comprise the computer program code which further comprises moving average code configured to implement a moving average along the PPG signal.

According to exemplary embodiments, the PPG signal indicates amounts of red light captured by the video.

According to exemplary embodiments, the portion of the skin is located at a finger of a user of the mobile phone.

BRIEF DESCRIPTION OF THE DRAWINGS

Further features, nature, and various advantages of the disclosed subject matter will be more apparent from the following detailed description and the accompanying drawings in which.

DETAILED DESCRIPTION

Figure 1:
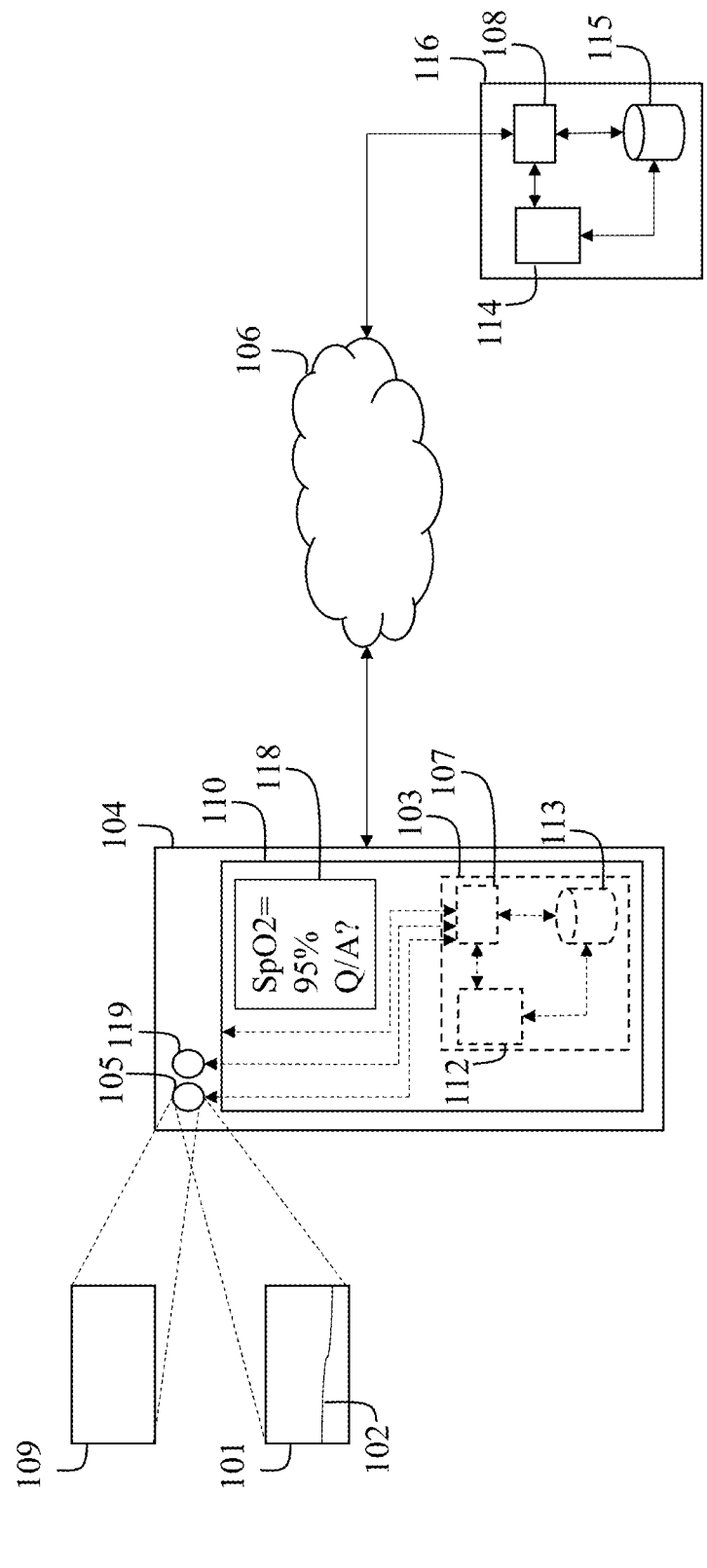
FIG. 1 is a schematic illustration of a simplified block diagram of a system in accordance with embodiments.

FIG. 1 is an illustration of a simplified block diagram of a system 100 in accordance with embodiments.

There is illustrated in FIG. 1 a mobile phone 104 having various circuitry 103 and a camera 105. The camera 105 is illustrated on a same side of the mobile phone 104 as a display 110 of the mobile phone, but it will be understood that the camera 105 may be located otherwise, such as on an opposite or an other side of the mobile phone 104 than the display 110.

The circuitry 103 includes an interface 103, a processor 112, and a memory 113, and the circuitry 103 is interconnected with the camera 105, a light source 119, and the display 110. Other interconnection schemes are covered herein as would be understood by one of ordinary skill in the art.

FIG. 1 also illustrates that the mobile phone 104 is connectable to a network 106 and also that such network is similarly connectable to a server 116 similarly having circuitry such as an interface 108, a processor 114, and a memory 115. Such networked connections may be via various internet connections including one or more of mobile networks and local networks.

FIG. 1 illustrates a simplified view of a cross-section of skin 101 having various vasculature 102. The vasculature 102 may carry blood, and through periodic pulses or otherwise, the blood may circulate through a body having the skin. The mobile phone 104 is configured to capture video of various parameters related to such circulation. For example, the camera 105 may be placed, depending on the mobile phone 104, sufficiently close to or in contact with the skin 101 and so as to record one or more of the parameters related to circulation, such as visible light or otherwise.

For example, as the blood carries cells, such as oxygenated hemoglobin and deoxygenated, lights, such as red light and infrared light, with respect to of the skin 101 may periodically change, and such change may be recorded via video capture through the camera 105 with or without the aid of illumination from the light source 119 which may be one or more light emitting diodes.

Figure 3B:
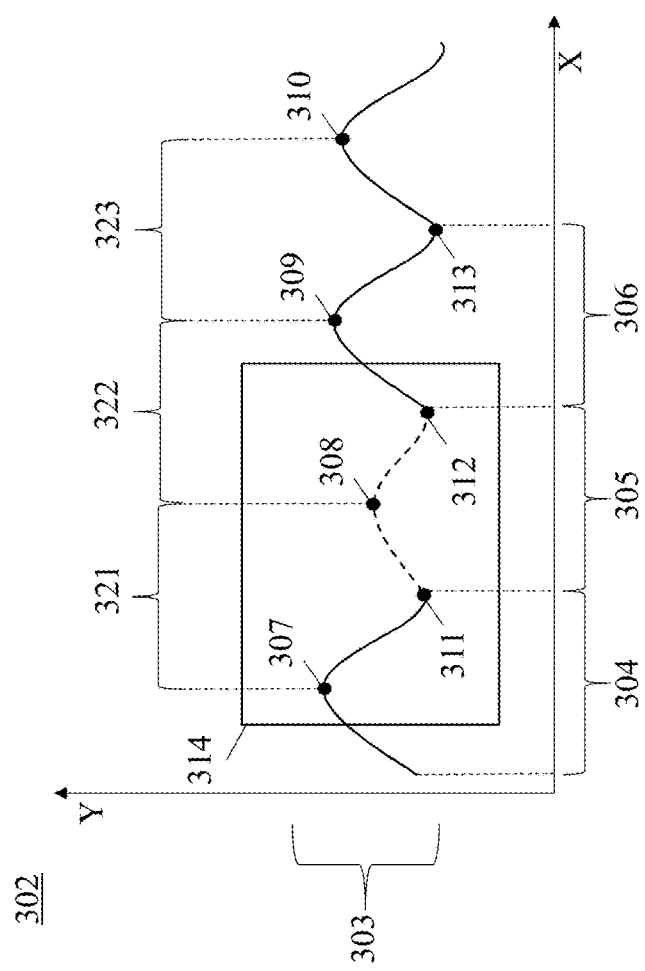
FIG. 3B is a schematic illustration of a simplified graph diagram in accordance with embodiments.
Figure 3A:
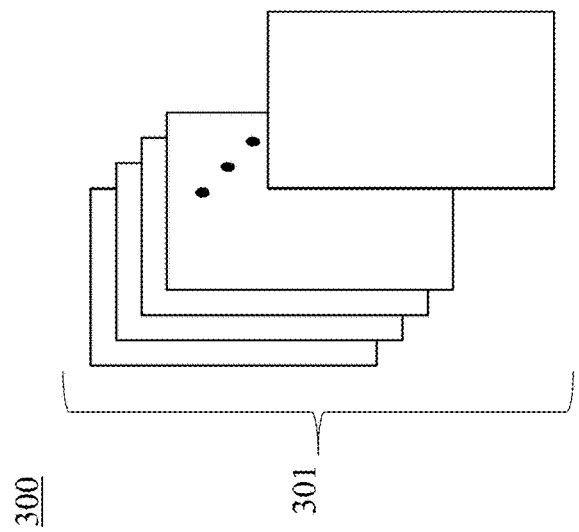
FIG. 3A is a schematic illustration of a simplified block diagram in accordance with embodiments.

The video, such as frames 301 shown in the diagram 300 of FIG. 3A, captured from the skin 101 may be analyzed by an app or a miniprogram of an app. For example, a web embedded architecture of many social media apps allows a miniprogram to be distributed easily: easy to reach to the users, easy to be deployed on user's mobile phone even without installations. However, the accessibility of the native video capture functionality of a mobile phone, and the ability to analyze the video in real time (e.g., 30 fps) pose compatibility and computation challenges to the miniprogram. Embodiments improve over such problems by deploying the miniprogram on an app platform, such as the WeChat platform, that is widely available to mobile phones and the latter by employing high performance analysis, including sampling such as described below.

With respect to sampling, since the PPG signals are obtained by placing one or more fingers on the camera 105 of the mobile phone 104, the acquired signals may not be stable due to the unstable measuring process, such as shaking or non-constant finger pressure at or near the skin 101. Therefore, to mitigate the effects of unstable signals on SpO2 measurement accuracy, the quality of the captured PPG signals is assessed first, and only the properly sampled data are selected for downstream processing.

Further, with respect to SpO2 measurement, although pulse oximeters may measure SpO2 based on the different absorbance of oxygenated hemoglobin and deoxygenated hemoglobin for red and infrared lights. However, if the infrared lights are filtered out by the camera 105 of the mobile phone 104 according to embodiments, such embodiments may instead we use RGB lights from the obtained PPG signals with respect to the obtained video to estimate SpO2. Calibration and moving average strategies may be applied to remove noisy data and increase the data quality.

As described below, various processing may be carried out at the mobile phone 104 and various processing may be carried out at the server 116 in providing SpO2 measurement and recommendations. The mobile phone 104 may access the miniprogram through the social media app via searching in the app or via scanning a code 109, such a barcode, QR code, or other recognizable symbol or symbols.

According to embodiments, the miniprogram architecture follows a model-view-viewmodel (MVVM), where a data model drives a display, such as at the display 110 of the mobile phone 104 and user interaction interface. The viewer model serves the UI views through the data binding, and an analysis of the frame by frame video is performed on the mobile phone 104 and signal processing, sampling and SpO2 calculation are performed in realtime with different frequencies.

Figure 2:
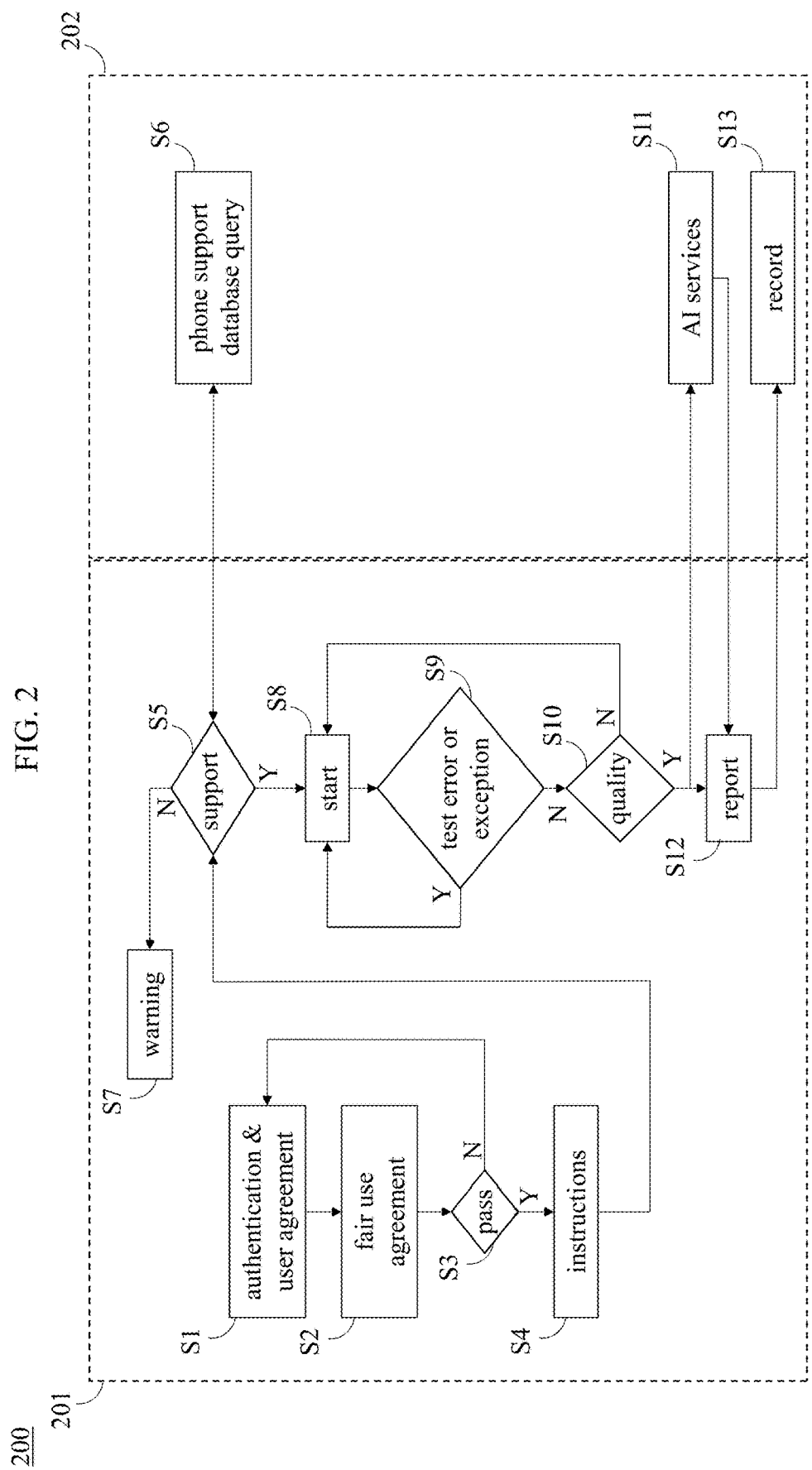
FIG. 2 is a schematic illustration of a simplified flow chart of systems in accordance with embodiments.

FIG. 2 is a schematic illustration of a simplified flow chart of systems in accordance with embodiments which uses a MVVM According to embodiments, the steps 201 may be performed by the miniprogram, and the steps 202 may be performed by one or more various cloud services to which the mobile phone 104 and or the server 116 may be connected.

At S1, the mobile phone 104 has attempted to access the miniprogram such as searching through the social media app, such as WeChat, or by scanning the code 109, and the user of the mobile phone 104 may ask for authentication and user agreement according to terms of the miniprogram. At S2, a fair use agreement may be displayed to the user, and at S3, if it is determined that the terms included in S1 and S2 have been accepted, then the mobile phone 104 may provide instructions to the user, such as any of audio guidance and a display of instructions on the display 110, and may await instructions from the user regarding whether to attempt to implement an SpO2 measurement.

At S5, the user of the mobile phone 104 has requested the miniprogram to implement an SpO2 measurement or has requested that the miniprogram determine whether the mobile phone 104 supports implementation of the SpO2 measurement.

At S6, the miniprogram has transmitted a request to cloud services to determine whether the mobile phone 104 supports implementation of the SpO2 measurement, and the cloud services query, as a phone support database query, whether the mobile phone 104 is capable of implementing the SpO2 measurement. For example, the mobile phone 104 or the server 116 may transmit one or more identifying parameters, such as a model of the move phone 104, data of one or more hardware components of the mobile phone 104, and may transmit one or more operating parameters of the mobile phone 104, such as video capture frames per second, fps, video quality, available battery, among other parameters.

At S7, if the cloud services have determined that the mobile phone 104 is not compatible with implementing the SpO2 measurements, a transmission back of such indication is provided miniprogram and to the mobile phone 104 which then outputs a warning, such as an audible or display information, indicating that the mobile phone 104 is not compatible with implementing the SpO2 measurement.

At S8, if the cloud services determined that the mobile phone 104 is compatible with implementing the SpO2 measurement, a transmission back of such indication is provided to the miniprogram which then proceeds with implementing the SpO2 measurement.

At S9, the miniprogram has attempted to gather video data as described herein and determines, through the miniprogram for example, whether one or more test errors or exceptions may have occurred, and if not, then the process proceeds to S10 where the miniprogram, determines whether a quality of the video data obtained satisfies a predetermined criteria. If a result of no is reached at any of S9 and S10, then the process may return to S8. Such steps S9 and S10 may be implemented by the miniprogram at the mobile phone 104 or one or more pieces of data obtained by the mobile phone 104 may be transmitted with respect to the miniprogram to the server 116 or other cloud services for such implementation.

FIG. 3B is a schematic illustration of a simplified graph diagram 302 in accordance with embodiments. The graph diagram 302 includes a PPG signal 303, and one or more such signal may be used according to embodiments, obtained from the video data captured by the camera 105 of the mobile phone, and at S9, since the PPG signal 303, from the video, may be periodic, an assessment of the data quality may be based on a number of peaks, such as peaks 307, 308, 309, 310, in a given period, such as any one or more of periods 305, 305, 306, 321, 322, and 323, as well as a variance of the peaks, such as peaks 307, 308, 309, 310, a variance of the valleys, such as valleys 311, 312, 313, or a combination of a variance between any of such peaks and valleys. The PPG signal 303 may correspond to one or more frequencies of light, such as an intensity of red light plotted on the Y-axis over time on the X-axis of the diagram 302. The red light may be a specific wavelength of light, such as a wavelength from 625-740 nm, or a range of wavelengths. Such variances will be understood as statistical measures with respect to how far apart individual values may be from an average of the set of those values, and the distribution shown in FIG. 3B is merely for illustrative purposes as other distributions may also be obtained depending on factors such as the mobile phone parameters, user parameters such as health, and handling of the mobile phone 104 during implementation through the miniprogram. Also, if a number of the peaks, such as peaks 307, 308, 309, 310, is less than the expected number during one or more of the periods 304, 305, 306, 321, 322, 323, then the PPG signal 303 in that period is deemed to be low quality, and thus is discarded, and other portions outside of that period may be retained for analysis. Likewise, if the variances are larger than a certain threshold, such PPG signal or a portion thereof, such as within any of the periods 304, 305, 306, 321, 322, 323 signals are also rejected or removed from analysis of the PPG signal 303. For example, the period 305 may be removed from the analysis as of a low quality as having a variance greater than some threshold with respect to one or more others of the periods 304 and 306. The thresholds of the number of peaks and their variances are empirically determined. Further, a moving average may be taken such that, for example, the window 314 may be averaged and moved along the PPG signal 303 which may reduce a data burden and possibly smooth the PPG signal 303. As such, data quality may be improved.

According to exemplary embodiments, the miniprogram, at S11, has transmitted a result of the processing of the PPG signal 303 to cloud services which may then implement AI services with respect to analyzing the received data. However, S11 may be skipped and the process may flow directly from S10 to S12 depending on the miniprogram.

At S12, an output result of the above analysis may be displayed at the display 110 of the mobile phone 104 through the miniprogram. The results, such as results 118, may indicate the SpO2 values directly to the user, and the results 118 may include a request for various patient diagnostic questions with respect to the SpO2 values and or may provide a recommendation to the user of the mobile phone 104.

Further, at S13, the results 118 may be stored, along with any of the PPG signal 303 data, by the cloud services.

The combination of the symptom check and SpO2 measurement chronically brings the gap closer between online medical diagnosis and general public, and the delivery of the miniprogram through social media app will make the gap even smaller. Embodiments described herein provide a quick estimate of SpO2 which may be further extended with symptom QA models for further medical assistive diagnosis.

The exemplary MVVM design of the miniprogram allows for extended functionalities by addition of more modules without architectural changes, eventually making the mobile phone 104 as a handy toolbox to access medical responder tools to improve the knowledge of the general public, reduce the misdiagnoses, alleviate mis-communication and conflicts between the patients and healthcare professionals, if any, and improve the public health, with possible profits on from advertising or online diagnoses.

Embodiments described herein can be used as a preliminary SpO2 measurement for monitoring SpO2 changes over time that may reveal indications for health-related conditions, which otherwise may or may not be noticeable. For anyone with a modern mobile phone and a social media app, they can scan a barcode and launch the miniprogram without additional hardware. Such embodiments enable users do a simple and quick test for SpO2 level and provides possible recommendations if needed.

The techniques described above, can be implemented as computer software using computer-readable instructions and physically stored in one or more computer-readable media or by a specifically configured one or more hardware processors. For example, FIG. 4 shows a computer system 400 suitable for implementing certain embodiments of the disclosed subject matter.

The computer software can be coded using any suitable machine code or computer language, that may be subject to assembly, compilation, linking, or like mechanisms to create code comprising instructions that can be executed directly, or through interpretation, micro-code execution, and the like, by computer central processing units (CPUs), Graphics Processing Units (GPUs), and the like.

The instructions can be executed on various types of computers or components thereof, including, for example, personal computers, tablet computers, servers, smartphones, gaming devices, internet of things devices, and the like.

Figure 4:
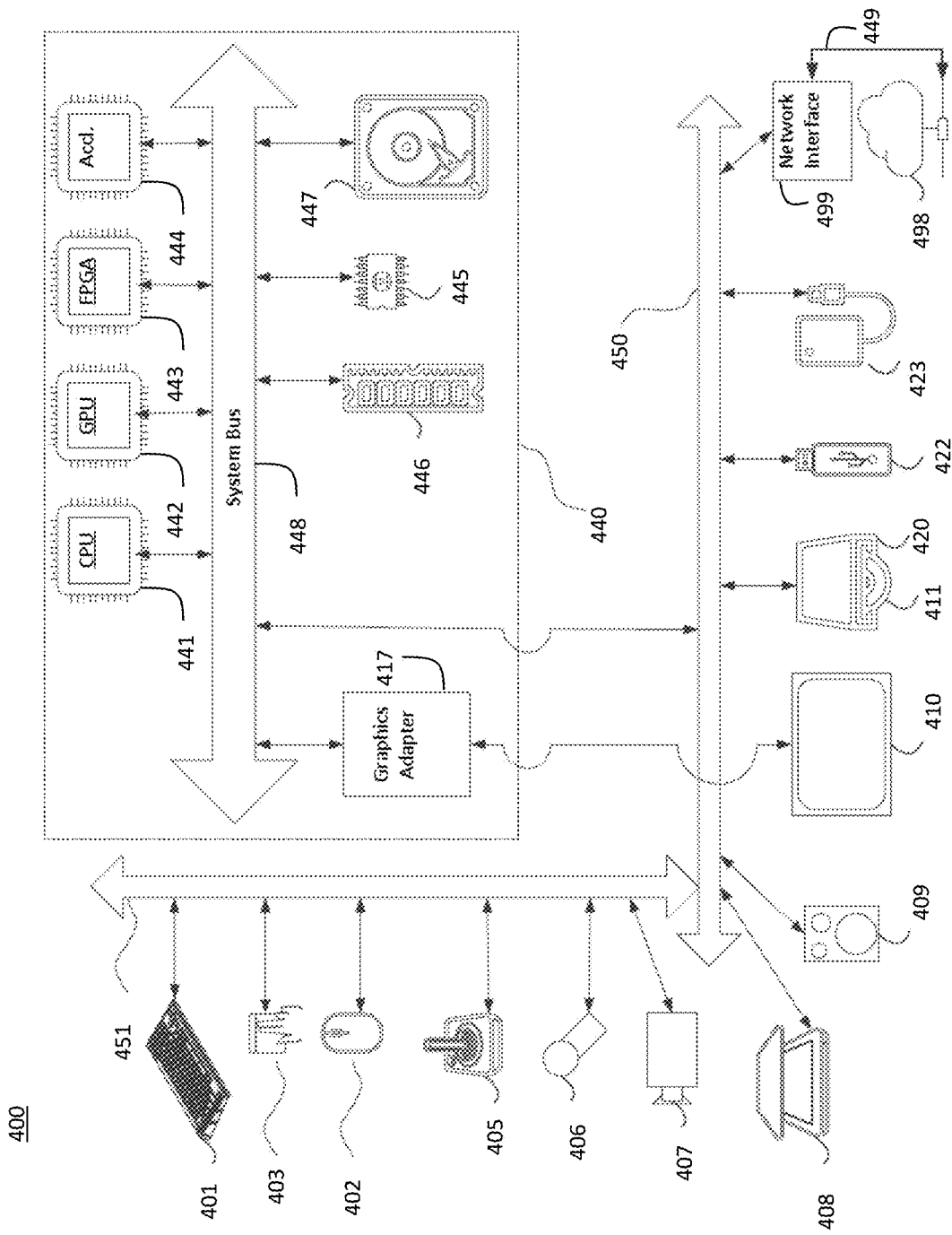
FIG. 4 is a schematic illustration of a simplified block diagram of system in accordance with embodiments.

The components shown in FIG. 4 for computer system 400 are exemplary in nature and are not intended to suggest any limitation as to the scope of use or functionality of the computer software implementing embodiments of the present disclosure. Neither should the configuration of components be interpreted as having any dependency or requirement relating to any one or combination of components illustrated in the exemplary embodiment of a computer system 400.

Computer system 400 may include certain human interface input devices. Such a human interface input device may be responsive to input by one or more human users through, for example, tactile input (such as: keystrokes, swipes, data glove movements), audio input (such as: voice, clapping), visual input (such as: gestures), olfactory input (not depicted). The human interface devices can also be used to capture certain media not necessarily directly related to conscious input by a human, such as audio (such as: speech, music, ambient sound), images (such as: scanned images, photographic images obtain from a still image camera), video (such as two-dimensional video, three-dimensional video including stereoscopic video).

Input human interface devices may include one or more of (only one of each depicted): keyboard 401, mouse 402, trackpad 403, touch screen 410 (such as the display 110), joystick 405, microphone 406, scanner 408, camera 407.

Computer system 400 may also include certain human interface output devices. Such human interface output devices may be stimulating the senses of one or more human users through, for example, tactile output, sound, light, and smell/taste. Such human interface output devices may include tactile output devices (for example tactile feedback by the touch-screen 410, or joystick 405, but there can also be tactile feedback devices that do not serve as input devices), audio output devices (such as: speakers 409, headphones (not depicted)), visual output devices (such as screens 410 to include CRT screens, LCD screens, plasma screens, OLED screens, each with or without touch-screen input capability, each with or without tactile feedback capability—some of which may be capable to output two dimensional visual output or more than three dimensional output through means such as stereographic output; virtual-reality glasses (not depicted), holographic displays and smoke tanks (not depicted)), and printers (not depicted).

Computer system 400 can also include human accessible storage devices and their associated media such as optical media including CD/DVD ROM/RW 420 with CD/DVD 411 or the like media, thumb-drive 422, removable hard drive or solid state drive 423, legacy magnetic media such as tape and floppy disc (not depicted), specialized ROM/ASIC/PLD based devices such as security dongles (not depicted), and the like.

Those skilled in the art should also understand that term "computer readable media" as used in connection with the presently disclosed subject matter does not encompass transmission media, carrier waves, or other transitory signals.

Computer system 400 can also include interface 499 to one or more communication networks 498. Networks 498 can for example be wireless, wireline, optical. Networks 498 can further be local, wide-area, metropolitan, vehicular and industrial, real-time, delay-tolerant, and so on. Examples of networks 498 include local area networks such as Ethernet, wireless LANs, cellular networks to include GSM, 3G, 4G, 5G, LTE and the like, TV wireline or wireless wide area digital networks to include cable TV, satellite TV, and terrestrial broadcast TV, vehicular and industrial to include CANBus, and so forth. Certain networks 498 commonly require external network interface adapters that attached to certain general-purpose data ports or peripheral buses (450 and 451) (such as, for example USB ports of the computer system 400; others are commonly integrated into the core of the computer system 400 by attachment to a system bus as described below (for example Ethernet interface into a PC computer system or cellular network interface into a smartphone computer system). Using any of these networks 498, computer system 400 can communicate with other entities. Such communication can be uni-directional, receive only (for example, broadcast TV), uni-directional send-only (for example CANbusto certain CANbus devices), or bi-directional, for example to other computer systems using local or wide area digital networks. Certain protocols and protocol stacks can be used on each of those networks and network interfaces as described above.

Aforementioned human interface devices, human-accessible storage devices, and network interfaces can be attached to a core 440 of the computer system 400.

The core 440 can include one or more Central Processing Units (CPU) 441, Graphics Processing Units (GPU) 442, a graphics adapter 417, specialized programmable processing units in the form of Field Programmable Gate Areas (FPGA) 443, hardware accelerators for certain tasks 444, and so forth. These devices, along with Read-only memory (ROM) 445, Random-access memory 446, internal mass storage such as internal non-user accessible hard drives, SSDs, and the like 447, may be connected through a system bus 448. In some computer systems, the system bus 448 can be accessible in the form of one or more physical plugs to enable extensions by additional CPUs, GPU, and the like. The peripheral devices can be attached either directly to the core's system bus 448, or through a peripheral bus 449. Architectures for a peripheral bus include PCI, USB, and the like.

CPUs 441, GPUs 442, FPGAs 443, and accelerators 444 can execute certain instructions that, in combination, can make up the aforementioned computer code. That computer code can be stored in ROM 445 or RAM 446. Transitional data can be also stored in RAM 446, whereas permanent data can be stored for example, in the internal mass storage 447. Fast storage and retrieval to any of the memory devices can be enabled through the use of cache memory, that can be closely associated with one or more CPU 441, GPU 442, mass storage 447, ROM 445, RAM 446, and the like.

The computer readable media can have computer code thereon for performing various computer-implemented operations. The media and computer code can be those specially designed and constructed for the purposes of the present disclosure, or they can be of the kind well known and available to those having skill in the computer software arts.

As an example and not by way of limitation, the computer system having architecture 400, and specifically the core 440 can provide functionality as a result of processor(s) (including CPUs, GPUs, FPGA, accelerators, and the like) executing software embodied in one or more tangible, computer-readable media. Such computer-readable media can be media associated with user-accessible mass storage as introduced above, as well as certain storage of the core 440 that are of non-transitory nature, such as core-internal mass storage 447 or ROM 445. The software implementing various embodiments of the present disclosure can be stored in such devices and executed by core 440. A computer-readable medium can include one or more memory devices or chips, according to particular needs. The software can cause the core 440 and specifically the processors therein (including CPU, GPU, FPGA, and the like) to execute particular processes or particular parts of particular processes described herein, including defining data structures stored in RAM 446 and modifying such data structures according to the processes defined by the software. In addition or as an alternative, the computer system can provide functionality as a result of logic hardwired or otherwise embodied in a circuit (for example: accelerator 444), which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

While this disclosure has described several exemplary embodiments, there are alterations, permutations, and various substitute equivalents, which fall within the scope of the disclosure. It will thus be appreciated that those skilled in the art will be able to devise numerous systems and methods which, although not explicitly shown or described herein, embody the principles of the disclosure and are thus within the spirit and scope thereof.

What is claimed is:

1. An apparatus comprising:
    at least one memory configured to store computer program code; and
    at least one hardware processor configured to access said computer program code and operate as instructed by said computer program code, said computer program code including:
    video capture code configured to cause the at least one hardware processor to control a camera of a mobile phone to capture a video of at least a portion of skin;
    extraction code configured to cause the at least one hardware processor to extract at least one photoplethysmogram (PPG) signal from the video;
    analysis code configured to cause the at least one hardware processor to implement a statistical processing of the PPG signal and to remove a portion of the PPG signal based on determining the portion to be noisy data by comparing a result of the statistical processing to at least one predetermined threshold;
    determination code configured to cause the at least one hardware processor to determine a peripheral oxygen saturation (SpO2) value based on the PPG signal, after the portion is removed from the PPG signal, with respect to a blood flow at the portion of skin; and
    display code configured to cause the at least one hardware processor to control a display of the mobile phone to display the SpO2 value.

2. The apparatus according to claim 1,
    wherein the computer program code further comprises social media app code configured to cause the at least one hardware processor to request a miniprogram from an external server,
    wherein the miniprogram comprises the video capture code, the extraction code, the determination code, and the display code.

3. The apparatus according to claim 2, wherein computer program code further comprises scanning code configured to cause the at least one hardware process to control the camera to scan a code and to implement, in response to scanning the code, the social media app code configured to cause the at least one hardware processor to request the miniprogram from an external server.

4. The apparatus according to claim 2, wherein the miniprogram comprises a model-view-viewmodel (MVVM).

5. The apparatus according to claim 1, wherein the statistical processing of the PPG signal further comprises altering, other than removing the portion, the PPG signal based on the result of the statistical processing.

6. The apparatus according to claim 1, wherein the statistical processing comprises determining a number of at least one of peaks and valleys of the PPG signal within a predetermined time among a plurality of frames of the video.

7. The apparatus according to claim 1, wherein the statistical processing comprises determining a variance of at least one of a peak and a valley of the PPG signal among a plurality of peaks and valleys of the PPG signal within a predetermined time among the plurality of frames of the video.

8. The apparatus according to claim 1, wherein the statistical processing comprises implementing a moving average along the PPG signal.

9. The apparatus according to claim 1, wherein the PPG signal indicates amounts of red light captured by the video.

10. The apparatus according to claim 1, wherein the portion of the skin is located at a finger of a user of the mobile phone.

11. A method performed by at least one computer processor comprising:
    controlling a camera of a mobile phone to capture a video of at least a portion of skin;
    extracting at least one photoplethysmogram (PPG) signal from the video;
    statistically processing the PPG signal and removing a portion of the PPG signal based on determining the portion to be noisy data by comparing a result of the statistical processing to at least one predetermined threshold; determining a peripheral oxygen saturation (SpO2) value based on the PPG signal, after the portion is removed from the PPG signal, with respect to a blood flow at the portion of skin; and
    controlling a display of the mobile phone to display the SpO2 value.

12. The method according to claim 11, further comprising requesting a miniprogram from an external server.

13. The method according to claim 11, further comprising:
    controlling the camera to scan a code; and
    to request, in response to scanning the code, the miniprogram from an external server.

14. The method according to claim 12, wherein the miniprogram comprises a model-view-viewmodel (MVVM).

15. The method according to claim 11,
    wherein the statistical processing of the PPG signal further comprises altering, other than removing the portion, the PPG signal based on the result of the statistical processing.

16. The method according to claim 11, wherein the statistical processing comprises determining a number of at least one of peaks and valleys of the PPG signal within a predetermined time among a plurality of frames of the video.

17. The method according to claim 11, wherein the statistical processing comprises determining a variance of at least one of a peak and a valley of the PPG signal among a plurality of peaks and valleys of the PPG signal within a predetermined time among the plurality of frames of the video.

18. The method according to claim 11, wherein the statistical processing comprises implementing a moving average along the PPG signal.

19. The method according to claim 11, wherein the PPG signal indicates amounts of red light captured by the video.

20. A non-transitory computer readable medium storing a program causing a computer to execute a process, the process comprising:
    controlling a camera of a mobile phone to capture a video of at least a portion of skin;
    extracting at least one photoplethysmogram (PPG) signal from the video;
    statistically processing the PPG signal and removing a portion of the PPG signal based on determining the portion to be noisy data by comparing a result of the statistical processing to at least one predetermined threshold;

determining a peripheral oxygen saturation (SpO2) value based on the PPG signal, after the portion is removed from the PPG signal, with respect to a blood flow at the portion of skin; and controlling a display of the mobile phone to display the SpO2 value.

\* \* \* \* \*